(12) United States Patent
Ishihara

(10) Patent No.: US 8,818,062 B2
(45) Date of Patent: Aug. 26, 2014

(54) FLUOROSCOPY DEVICE

(71) Applicant: Olympus Corporation, Tokyo (JP)

(72) Inventor: Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 94 days.

(21) Appl. No.: 13/645,083

(22) Filed: Oct. 4, 2012

(65) Prior Publication Data

US 2013/0028501 A1    Jan. 31, 2013

Related U.S. Application Data

(63) Continuation of application No. PCT/JP2011/058758, filed on Apr. 7, 2011.

(30) Foreign Application Priority Data

Apr. 7, 2010 (JP) ................................ 2010-088740

(51) Int. Cl.
G06K 9/00 (2006.01)
A61B 6/00 (2006.01)

(52) U.S. Cl.
CPC ...................................... A61B 6/504 (2013.01)
USPC .......................................................... 382/128

(58) Field of Classification Search
None
See application file for complete search history.

(56) References Cited

U.S. PATENT DOCUMENTS 5,590,660 A * 1/1997 MacAulay et al. ............ 600/478
8,421,034 B2 * 4/2013 Ono ............................ 250/458.1
2005/0027166 A1 * 2/2005 Matsumoto et al. .......... 600/162
2005/0153356 A1 * 7/2005 Okawa et al. ...................... 435/6
2008/0232548 A1 * 9/2008 Tanaka ......................... 378/98.2

FOREIGN PATENT DOCUMENTS

| JP | 62-247232 A | 10/1987 |
| JP | 03-058729 A | 3/1991 |
| JP | 5-228108 A | 9/1993 |
| JP | 6-284294 A | 10/1994 |
| JP | 08-224209 A | 9/1996 |
| JP | 2001-137172 A | 5/2001 |
| JP | 2001-137173 A | 5/2001 |
| JP | 2003-036436 A | 2/2003 |
| JP | 2005-348902 A | 12/2005 |
| JP | 2006-061683 A | 3/2006 |
| JP | 2006-175052 A | 7/2006 |
| JP | 2007-117351 A | 5/2007 |
| JP | 2008-173290 A | 7/2008 |

OTHER PUBLICATIONS

International Search Report dated Jun. 28, 2011 issued in PCT/JP2011/058758.

* cited by examiner

Primary Examiner — Hadi Akhavannik
(74) Attorney, Agent, or Firm — Scully, Scott, Murphy & Presser, P.C.

(57) ABSTRACT

A fluoroscopy device includes a light source that irradiates an observation site with excitation light and white light; a fluorescence-image generating section that acquires a fluorescence image by capturing fluorescence generated in the observation site irradiated with the excitation light; a reference-image generating section that acquires a reference image by capturing return light returning from the observation site irradiated with the white light; an observation-condition determining section that determines the observation conditions of the observation site on the basis of the reference image acquired by the reference-image generating section; a preprocessing section that corrects gradation values of the reference image on the basis of the observation conditions of the observation site; and a fluorescence-image correcting section that generates a corrected fluorescence image by dividing the fluorescence image acquired by the fluorescence-image generating section by the reference image whose gradation values have been corrected by the preprocessing section.

17 Claims, 11 Drawing Sheets

FLUOROSCOPY DEVICE

CROSS REFERENCE TO RELATED APPLICATIONS

This is a continuation of International Application PCT/JP/2011/058758, with an international filing date of Apr. 7, 2011, which is hereby incorporated by reference herein in its entirety. This application claims the benefit of Japanese Patent Application No. 2010-088740, the content of which is incorporated herein by reference.

TECHNICAL FIELD

The present invention relates to fluoroscopy devices.

BACKGROUND ART

A known fluoroscopy device in the related art radiates excitation light, which generates fluorescence by exciting a fluorescent agent that preferentially accumulates in a lesion, such as cancer cells, onto an observation site that is administered the fluorescent agent. The fluoroscopy device photographs the generated fluorescence so as to acquire a fluorescence image of the lesion (for example, see Patent Literatures 1 to 3).

The fluoroscopy device discussed in each of Patent Literatures 1 to 3 divides the fluorescence image based on the intensity of the fluorescence generated in the observation site irradiated with the excitation light by a reference image based on the intensity of return light returning from the same observation site irradiated with white light so as to correct a variation in fluorescence intensity, which is dependent on the observation distance, the observation angle, etc., in the fluorescence image.

CITATION LIST

Patent Literature

{PTL 1} Japanese Unexamined Patent Application, Publication No. Sho 62-247232
{PTL 2} Japanese Examined Patent Application, Publication No. Hei 3-058729
{PTL 3} Japanese Unexamined Patent Application, Publication No. 2006-175052

SUMMARY OF INVENTION

The present invention employs the following solutions.

A first aspect of the present invention provides a fluoroscopy device including a light source that irradiates a subject with excitation light and reference light; a fluorescence-image acquisition section that acquires a fluorescence image by capturing fluorescence generated in the subject irradiated with the excitation light from the light source; a reference-image acquisition section that acquires a reference image by capturing return light returning from the subject irradiated with the reference light from the light source; an observation-condition determining section that determines an observation condition of the subject on the basis of the reference image acquired by the reference-image acquisition section; a gradation-value correcting section that corrects gradation values of the reference image acquired by the reference-image acquisition section on the basis of the observation condition of the subject determined by the observation-condition determining section; and a corrected-fluorescence-image generating section that generates a corrected fluorescence image by dividing the fluorescence image acquired by the fluorescence-image acquisition section by the reference image whose gradation values have been corrected by the gradation-value correcting section.

A second aspect of the present invention provides a fluoroscopy device including a light source that irradiates a subject with excitation light and reference light; a fluorescence-image acquisition section that acquires a fluorescence image by capturing fluorescence generated in the subject irradiated with the excitation light from the light source; a reference-image acquisition section that acquires a reference image by capturing return light returning from the subject irradiated with the reference light from the light source; an observation-condition determining section that determines an observation condition of the subject on the basis of the reference image acquired by the reference-image acquisition section; a gradation-value correcting section that corrects gradation values of the fluorescence image acquired by the fluorescence-image acquisition section on the basis of the observation condition of the subject determined by the observation-condition determining section; and a corrected-fluorescence-image generating section that generates a corrected fluorescence image by dividing the fluorescence image, whose gradation values have been corrected by the gradation-value correcting section, by the reference image acquired by the reference-image acquisition section.

A third aspect of the present invention provides a fluoroscopy device including a light source that irradiates a subject with excitation light and reference light; a fluorescence-image acquisition section that acquires a fluorescence image by capturing fluorescence generated in the subject irradiated with the excitation light from the light source; a reference-image acquisition section that acquires a reference image by capturing return light returning from the subject irradiated with the reference light from the light source; an observation-condition determining section that determines an observation condition of the subject on the basis of the reference image acquired by the reference-image acquisition section; a gradation-value correcting section that corrects gradation values of the reference image acquired by the reference-image acquisition section and the fluorescence image acquired by the fluorescence-image acquisition section on the basis of the observation condition of the subject determined by the observation-condition determining section; and a corrected-fluorescence-image generating section that generates a corrected fluorescence image by dividing the fluorescence image, whose gradation values have been corrected by the gradation-value correcting section, by the reference image whose gradation values have been corrected by the gradation-value correcting section.

A fourth aspect of the present invention provides a fluoroscopy device including a light source that irradiates a subject with excitation light and reference light; a fluorescence-image acquisition section that acquires a fluorescence image by capturing fluorescence generated in the subject irradiated with the excitation light from the light source; a reference-image acquisition section that acquires a reference image by capturing return light returning from the subject irradiated with the reference light from the light source; a corrected-fluorescence-image generating section that generates a corrected fluorescence image by dividing the fluorescence image acquired by the fluorescence-image acquisition section by the reference image acquired by the reference-image acquisition section; an observation-condition determining section that determines an observation condition of the subject on the basis of the reference image acquired by the reference-image acquisition section; and a gradation-value correcting section that corrects gradation values of the corrected fluorescence image generated by the corrected-fluorescence-image generating section on the basis of the observation condition of the subject determined by the observation-condition determining section.

In any one of the first to third aspects, the gradation-value correcting section may change at least one of a first exponent and a second exponent in accordance with the observation condition of the subject determined by the observation-condition determining section, the first exponent corresponding to gradation values of the fluorescence image acquired by the fluorescence-image acquisition section when the subject is irradiated with the excitation light and being obtained by power approximation of distance characteristics from the light source to the subject, the second exponent corresponding to gradation values of the reference image acquired by the reference-image acquisition section when the subject is irradiated with the reference light and being obtained by power approximation of the distance characteristics from the light source to the subject.

In the fourth aspect, the gradation-value correcting section may include a threshold-value setting section that sets a threshold value on the basis of an average value of the gradation values of pixels in the corrected fluorescence image generated by the corrected-fluorescence-image generating section, and an image adjusting section that increases the contrast in the corrected fluorescence image between an area having gradation values larger than the threshold value and an area having gradation values smaller than the threshold value. The threshold value may be changed in accordance with the observation condition of the subject determined by the observation-condition determining section.

In the first aspect, the gradation-value correcting section may include a low-pass filter that blocks a high-frequency component in the reference image acquired by the reference-image acquisition section. A frequency band to be blocked by the low-pass filter may be changed in accordance with the observation condition of the subject.

In any one of the first to fourth aspects, the observation-condition determining section may determine that the subject is viewed from a parallel position if gradation values of a central area in the reference image are smaller than or equal to a predetermined value, or may determine that the subject is viewed from the front if the gradation values of the central area in the reference image are larger than the predetermined value.

In any one of the first to fourth aspects, the gradation-value correcting section may include a storage section that stores a plurality of correction coefficients in correspondence with the observation condition of the subject. A correction coefficient to be used may be selected from among the plurality of correction coefficients stored in the storage section in accordance with the observation condition of the subject determined by the observation-condition determining section so as to correct gradation values of at least one of the reference image, the fluorescence image, and the corrected fluorescence image.

DESCRIPTION OF EMBODIMENTS

First Embodiment

A fluoroscopy device according to a first embodiment of the present invention will be described below with reference to the drawings.

Figure 1:
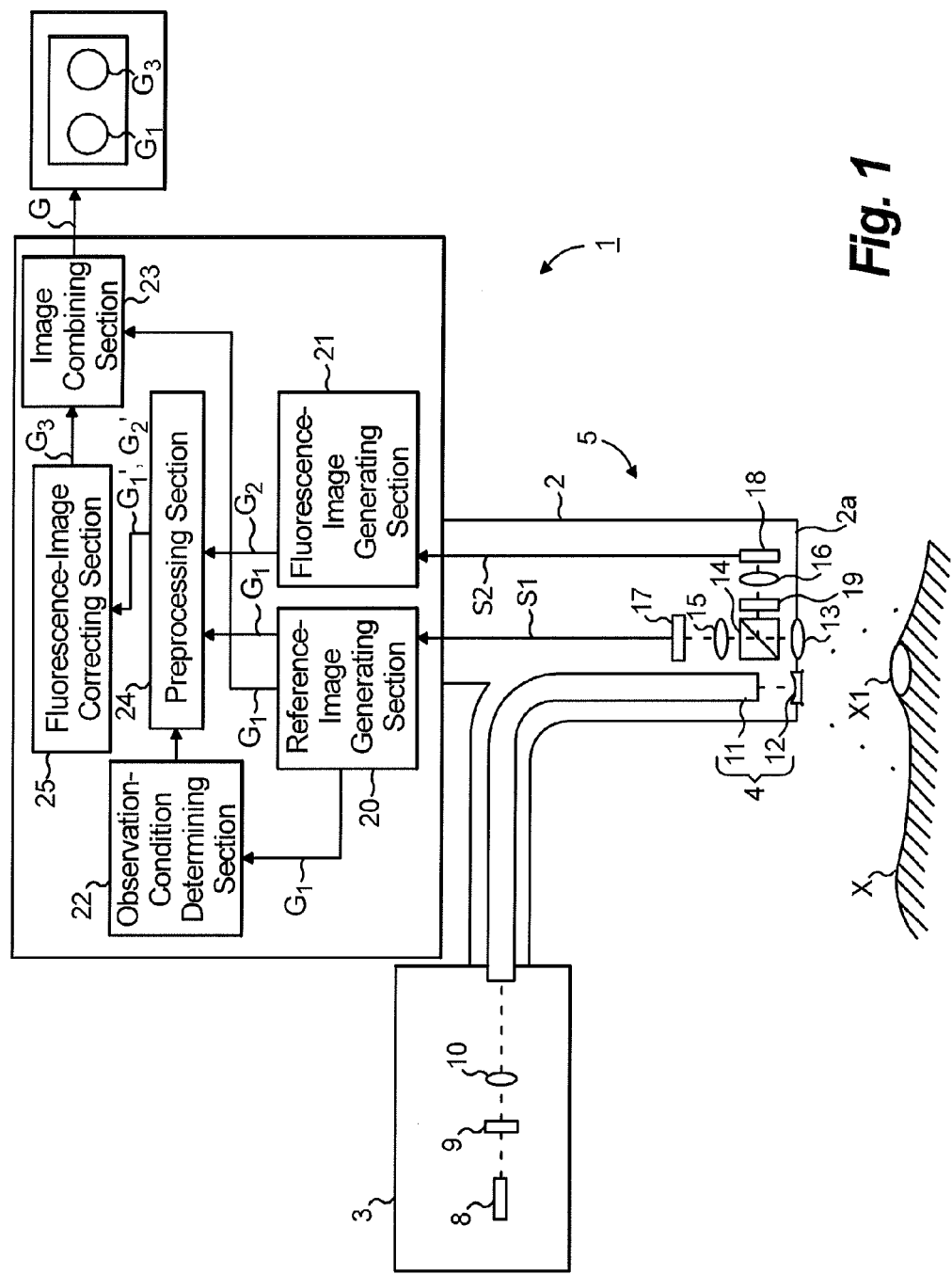
FIG. 1 schematically illustrates the configuration of a fluoroscopy device according to a first embodiment of the present invention.

As shown in FIG. 1, a fluoroscopy device 1 according to this embodiment is an endoscopic device and includes a narrow insertion section 2 to be inserted into a body, a light source 3, an illumination unit 4 that emits illumination light and excitation light from the light source 3 toward an observation site X from the tip of the insertion section 2, an image acquisition unit 5 that is provided at the tip of the insertion section 2 and acquires image information of biological tissue at the observation site X, an image processing section 6 that is disposed at the base end of the insertion section 2 and processes the image information acquired by the image acquisition unit 5, and a monitor 7 that displays an image G processed by the image processing section 6.

The light source 3 includes a xenon lamp 8, a filter 9 that transmits, for example, white light (reference light) and excitation light having a wavelength ranging between 400 nm and 740 nm included in illumination light generated by the xenon lamp 8, and a coupling lens 10 that focuses the white light and the excitation light transmitted through the filter 9.

The illumination unit 4 includes a light guide fiber 11 extending substantially along the entire length of the insertion section 2 and guiding the white light and the excitation light focused by the coupling lens 10, and an illumination optical system 12 that is provided at the tip of the insertion section 2 and spreads the white light and the excitation light guided by the light guide fiber 11 so as to radiate the light onto the observation site X facing an end surface 2a of the insertion section 2.

The image acquisition unit 5 includes an objective lens 13 that collects return light returning from a predetermined observation area of the observation site X; a dichroic mirror 14 that reflects light having an excitation wavelength or longer (i.e., excitation light and fluorescence) and transmits white light having a shorter wavelength than the excitation wavelength, which are included in the return light collected by the objective lens 13; two focusing lenses 15 and 16 that respectively focus the white light transmitted through the dichroic mirror 14 and the fluorescence reflected by the dichroic mirror 14; and two image acquisition elements 17 and 18, such as CCDs, that respectively acquire images of the fluorescence and the white light focused by the focusing lenses 15 and 16. In the drawing, reference numeral 19 denotes an excitation-light cut filter that blocks the excitation light from the light reflected by the dichroic mirror 14 (for example, only transmits light having a wavelength ranging between 760 nm and 850 nm).

The image processing section 6 includes a reference-image generating section (reference-image acquisition section) 20 that generates a reference image $G_1$, a fluorescence-image generating section (fluorescence-image acquisition section) 21 that generates a fluorescence image $G_2$, an observation-condition determining section 22 that determines the observation conditions of the observation site X, a preprocessing section (gradation-value correcting section) 24 that corrects gradation values of the reference image $G_1$ and the fluorescence image $G_2$, a fluorescence-image correcting section (corrected-fluorescence-image generating section) 25 that generates a corrected fluorescence image $G_3$ from the reference image $G_1$ and the fluorescence image $G_2$, and an image combining section 23 that generates a combined image G by combining the corrected fluorescence image $G_3$ with the reference image $G_1$.

The reference-image generating section 20 generates the reference image $G_1$ from reference-image information $S_1$ acquired by the image acquisition element 17.

The fluorescence-image generating section 21 generates the fluorescence image $G_2$ from fluorescence-image information $S_2$ acquired by the image acquisition element 18.

The fluorescence image $G_2$ may be, for example, a fluorescence image from fluorochrome Cy7. In particular, by preliminarily administering a tumor-specific fluorescent agent to the observation site X, a tumor-specific fluorescence image $G_2$ can be obtained. An example of such a tumor-specific fluorescent agent includes a fluorescent agent in which an antibody (anti-CEA-body) against a cancer-specific molecule CEA and fluorochrome Cy7 are bound to each other. As the reference image $G_1$, for example, an image based on return light obtained as a result of white light being reflected at the surface of the observation site X and return light obtained as a result of white light being scattered within the observation site X may be used.

Figure 2:
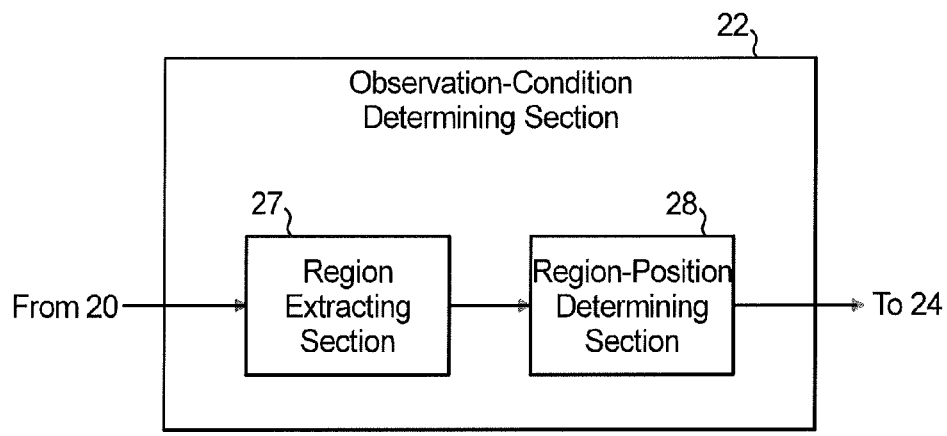
FIG. 2 is a functional block diagram of an observation-condition determining section in FIG. 1.

Referring to FIG. 2, the observation-condition determining section 22 includes a region extracting section 27 that extracts a region having gradation values smaller than or equal to a predetermined value from the reference image $G_1$ acquired by the reference-image generating section 20, and a region-position determining section 28 that determines the position of the region extracted by the region extracting section 27. With such a configuration, the observation-condition determining section 22 determines the observation conditions of the observation site X on the basis of the reference image $G_1$ acquired by the reference-image generating section 20.

Figure 3:
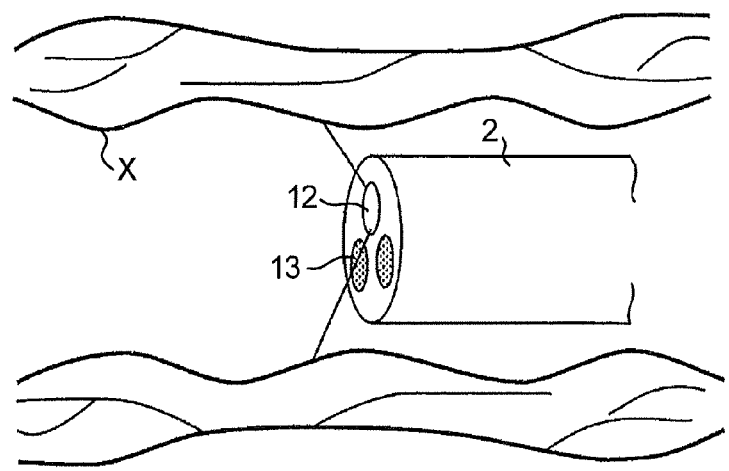
FIG. 3 illustrates a state where the large intestine is viewed from a parallel position.
Figure 4:
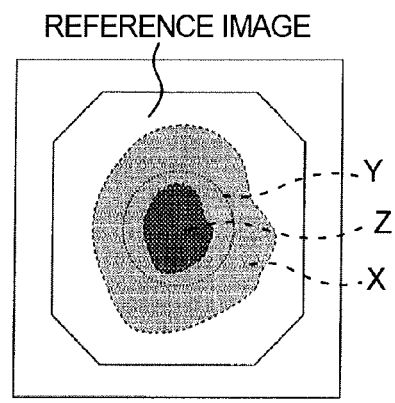
FIG. 4 illustrates a display example of a reference image in the state in FIG. 3.
Figure 5:
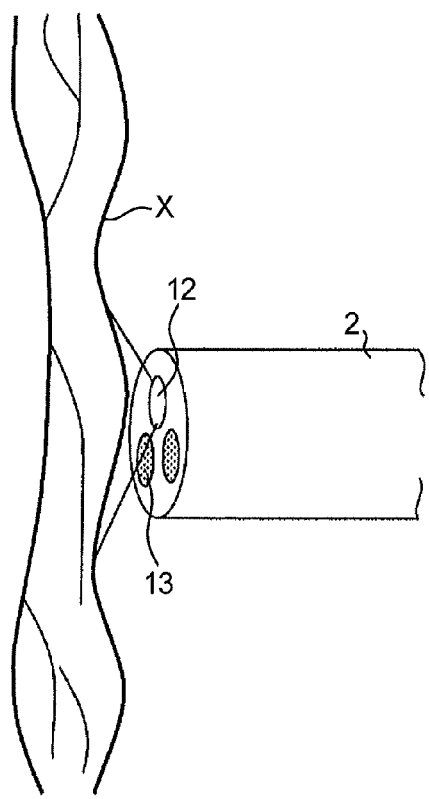
FIG. 5 illustrates a state where the large intestine is viewed from the front.
Figure 6:
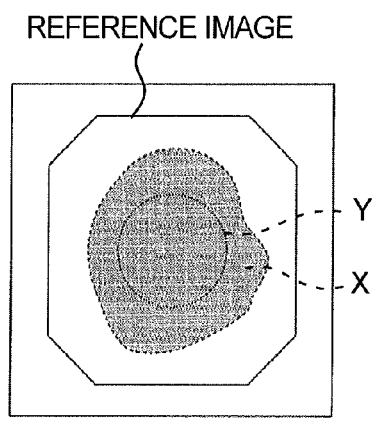
FIG. 6 illustrates a display example of a reference image in the state in FIG. 5.

Specifically, when the observation site X within, for example, the large intestine is viewed from a parallel position (namely, when the optical axis of the objective lens 13 is aligned with the axis of the large intestine), as shown in FIG. 3, a region Z with gradation values smaller than or equal to the predetermined value exists within a region Y surrounding the center of the reference image $G_1$, as shown in FIG. 4. On the other hand, when the observation site X is viewed from the front (namely, when the optical axis of the objective lens 13 intersects the axis of the large intestine), as shown in FIG. 5, the region Z with gradation values smaller than or equal to the predetermined value does not exist within the region Y surrounding the center of the reference image $G_1$, as shown in FIG. 6.

If the gradation values in the predetermined region Y surrounding the center of the reference image $G_1$ are smaller than or equal to the predetermined value, the observation-condition determining section 22 determines that the observation site X is viewed from a parallel position, as shown in FIG. 3. On the other hand, if the gradation values in the region Y surrounding the center of the reference image $G_1$ are larger than the predetermined value, the observation-condition determining section 22 determines that the observation site X is viewed from the front, as shown in FIG. 5.

Based on the observation conditions of the observation site X determined by the observation-condition determining section 22, the preprocessing section 24 corrects the gradation values of the reference image $G_1$ acquired by the reference-image generating section 20 so as to generate a reference image $G_1'$.

Furthermore, based on the observation conditions of the observation site X determined by the observation-condition determining section 22, the preprocessing section 24 corrects the gradation values of the fluorescence image $G_2$ generated by the fluorescence-image generating section 21 so as to generate a fluorescence image $G_2'$.

Specifically, the preprocessing section 24 has a storage section (not shown) that stores multiple correction coefficients in correspondence with the observation conditions of the observation site X, and selects a correction coefficient to be used from among the multiple correction coefficients stored in the storage section in accordance with the observation conditions of the observation site X determined by the observation-condition determining section 22 so as to correct the gradation values of the reference image $G_1$ and the fluorescence image $G_2$.

A detailed description of how image processing is performed by the preprocessing section 24 will be provided later.

The fluorescence-image correcting section 25 divides the fluorescence image $G_2'$, whose gradation values have been corrected by the preprocessing section 24, by the reference image $G_1'$, whose gradation values have been corrected by the preprocessing section 24, so as to generate the corrected fluorescence image $G_3$. Specifically, in the following example, the fluorescence-image correcting section 25 performs the following division for each pixel by using gradation values $FL_{after}$ of the preprocessed fluorescence image $G_2'$ and gradation values $RL_{after}$ of the preprocessed reference image $G_1'$ so as to acquire gradation values CL of the corrected fluorescence image $G_3$.

$$CL = FL_{after}/RL_{after}$$

The image combining section 23 combines the reference image $G_1$ generated by the reference-image generating section 20 with the corrected fluorescence image $G_3$ generated by the fluorescence-image correcting section 25. Specifically, for example, the image combining section 23 generates the combined image G in which the reference image $G_1$ and the corrected fluorescence image $G_3$ are arranged side-by-side, and outputs the combined image G to the monitor 7.

The monitor 7 displays the combined image G, that is, an image in which the reference image $G_1$ and the corrected fluorescence image $G_3$ are arranged side-by-side.

A detailed description of how image processing is performed by the preprocessing section 24 will be provided below.

The gradation values of the reference image $G_1'$ and the fluorescence image $G_2'$ generated by the preprocessing section 24 are expressed as follows:

$$FL_{after} = A_1 \times (A_2 \times FL_{before})^x \quad (1)$$

$$RL_{after} = B_1 \times (B_2 \times RL_{before})^y \quad (2)$$

where $FL_{before}$ denotes gradation values of the fluorescence image $G_2$ generated by the fluorescence-image generating section 21, $RL_{before}$ denotes gradation values of the reference image $G_1$ generated by the reference-image generating section 20, $FL_{after}$ denotes gradation values of the fluorescence image $G_2'$ whose gradation values have been corrected by the preprocessing section 24, $RL_{after}$ denotes gradation values of the reference image $G_1'$ whose gradation values have been corrected by the preprocessing section 24, $A_1$, $A_2$, $B_1$, and $B_2$ denote arbitrarily set constants, and x and y denote predetermined exponents.

The following description relates to how the exponents x and y are set.

Generally, the fluorescence image $G_2$ and the reference image $G_1$ substantially have the following dependencies relative to an observation distance D and an observation angle $\theta$:

$$FL_{before} \propto D^a \cos^b \theta, \; RL_{before} \propto D^c \cos^d \theta.$$

By dividing the above, the following relationship is obtained: $FL_{before}/RL_{before} \propto D^{a-c} \cos^{b-d}\theta$. The observation distance D is, for example, the distance from the tip of the insertion section 2 to the surface of the observation site X, and the observation angle $\theta$ is, for example, an angle formed between the normal to the surface of the observation site X and the optical axis of the objective lens 13 (or the longitudinal axis of the insertion section 2).

Next, when the gradation values of the fluorescence image $G_2$ and the reference image $G_1$ are raised to the power of the exponents x and y, respectively, the following relationship is obtained:

$$FL_{before}^x / RL_{before}^y \propto D^{ax-cy} \cos^{bx-dy} \theta.$$

In this case, assuming that $m = ax - cy$ and $n = bx - dy$, the exponents x and y are set such that m and n are allowable limits.

Specifically, the following relationships are obtained:

$$x = (cn - dm)/(bc - ad) \quad (3)$$

$$y = (an - bm)/(bc - ad). \quad (4)$$

If the denominator $(bc-ad)$ is equal to zero, the exponents x and y are set such that the following relationship is satisfied: $x:y = c:a = d:b$.

With regard to an assumed maximum observation distance $D_{max}$, an assumed minimum observation distance $D_{min}$, an assumed maximum observation angle $\theta_{max}$, and an assumed minimum observation angle $\theta_{min}$ ($0° \leq \theta_{min} < \theta_{max} \leq 90°$), ratios $r_D$ and $r_\theta$ are as follows:

$$r_D = D_{max}/D_{min}, \; r_\theta = \theta_{max}/\theta_{min}.$$

By using a maximum allowable error rate $e_{max}$ in a corrected fluorescence image, m and n are selected so that the following relationship is satisfied:

$$r_D^{|m|} \cdot r_\theta^{|n|} \leq 1 + e_{max}. \quad (5)$$

The range of the assumed observation distance D can be determined from, for example, the depth of field of the objective lens 13, and the range of the assumed observation angle $\theta$ can be determined from, for example, the field of view of the objective lens 13.

Furthermore, $e_{max}$ can be determined from the following computational equation:

$$(FL_{after}/RL_{after})_{max} \div (FL_{after}/RL_{after})_{min} = 1 + e_{max}.$$

Therefore, the maximum allowable error rate $e_{max}$ may first be set in advance, m and n that satisfy equation (5) may be subsequently set, and x and y that satisfy equation (3) and equation (4) may be set on the basis of m and n.

The exponents a to d are determined as follows.

Specifically, while changing the distance D from the illumination unit 4 to the observation site X, average values of gradation values in a predetermined area in each of the fluorescence image $G_2$ and the reference image $G_1$ acquired by radiating excitation light and white light onto the observation site X from the illumination unit 4 are plotted relative to the distance D. Accordingly, by power approximation of the obtained distance characteristics, namely, by regressing the obtained distance characteristics to a power function $D^a$ and a power function $D^c$, the exponent a and the exponent c that indicate the dependencies relative to the observation distance D are obtained.

The same applies to the exponents b and d relative to the observation angle $\theta$. Specifically, while changing the angle $\theta$ between the optical axis of the illumination unit 4 and the observation site X, average values of gradation values in a predetermined area in each of the fluorescence image $G_2$ and the reference image $G_1$ acquired by radiating excitation light and white light onto the observation site X from the illumination unit 4 are plotted relative to the cosine of the angle $\cos \theta$. Accordingly, by power approximation of the obtained cosine characteristics, namely, by regressing the obtained cosine characteristics to power functions $\cos^b \theta$ and $\cos^d \theta$, the exponents b and d that indicate the dependencies relative to the observation angle $\theta$ are obtained.

The exponents a and c indicating the dependencies with respect to the distance vary depending on the observation conditions. Specifically, absolute values of the exponents a and c ($a<0$, $c<0$) increase with decreasing observation distance D. Generally, the observation distance D is smaller when the observation site X is viewed from the front than when it is viewed from a parallel position. Therefore, when it is determined that the observation site X is viewed from the front, it can be assumed that the absolute values of the exponents a and c are larger than those when the observation site X is viewed from a parallel position. In particular, if an image of reflected light is used as the reference image, an increase in the absolute value of the exponent c when the distance decreases is also large.

The preprocessing section 24 changes the exponents a and c in accordance with the observation conditions of the observation site X determined by the observation-condition determining section 22. Specifically, if the observation-condition determining section 22 determines that the observation site X is viewed from the front, the preprocessing section 24 increases the absolute values of the exponents a and c. On the other hand, if the observation-condition determining section 22 determines that the observation site X is viewed from a parallel position, the preprocessing section 24 decreases the absolute values of the exponents a and c.

By setting appropriate correction parameters in accordance with the observation conditions in this manner, a corrected fluorescence image with a reduced variation in fluorescence intensity, which is dependent on the observation distance and the observation angle, is always generated.

Figure 7:
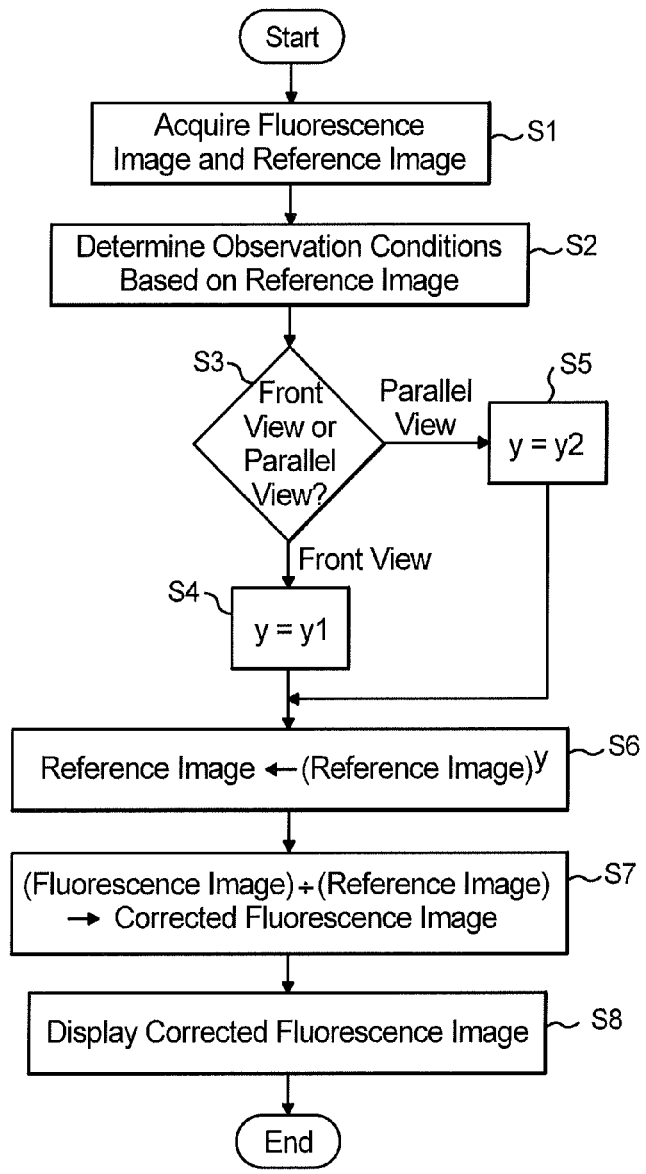
FIG. 7 is a flowchart illustrating a process performed by an image processing section in FIG. 1.

The operation of the fluoroscopy device 1 having the above-described configuration will be described below with reference to a flowchart shown in FIG. 7.

In order to observe the observation site X within the body cavity of a living organism by using the fluoroscopy device 1 according to this embodiment, a fluorescent agent, which preferentially accumulates in a lesion X1, such as cancer cells, is made to attach to or be absorbed in the observation site X. In this state, the observation site X is irradiated with excitation light so that the fluorescent agent is excited, whereby fluorescence is generated.

Subsequently, the insertion section 2 is inserted into the body cavity so as to make the tip 2a face the observation site X. In this state, the light source 3 is activated so that the white light including the excitation light generated from the xenon lamp 8 and transmitted by the filter 9 is focused by the coupling lens 10 and is guided to the tip 2a of the insertion section 2 by the light guide fiber 11. Then, the white light is spread by the illumination optical system 12 so as to irradiate the observation site X.

In the observation site X, a fluorescent material contained therein is excited by the excitation light so that fluorescence is generated, and the white light and the excitation light are partially reflected at the surface of the observation site X. The objective lens 13 collects the fluorescence, the white light, and the excitation light, and the dichroic mirror 14 reflects light having the excitation wavelength or longer, i.e., the excitation light and the fluorescence, and transmits the white light having a shorter wavelength than the excitation wavelength.

With regard to the excitation light and the fluorescence reflected by the dichroic mirror 14, the excitation light is removed by the filter 19 so that only the fluorescence is focused by the focusing lens 16, whereby the fluorescence is captured by the image acquisition element 18. Consequently, fluorescence-image information of the observation site X is acquired by image acquisition element 18. The white light transmitted through the dichroic mirror 14 is focused by the focusing lens 15 so as to be captured by the image acquisition element 17. Consequently, reference-image information of the observation site X is acquired by the image acquisition element 17. The fluorescence-image information and the reference-image information may be acquired at the same time or may be acquired in any order.

The fluorescence-image information acquired by the image acquisition element 18 and the reference-image information acquired by the image acquisition element 17 are respectively transmitted to the fluorescence-image generating section 21 and the reference-image generating section 20 in the image processing section 6.

A two-dimensional fluorescence image is generated in the fluorescence-image generating section 21 on the basis of the fluorescence-image information transmitted from the image acquisition element 18, and a two-dimensional reference image is generated in the reference-image generating section 20 on the basis of the reference-image information transmitted from the image acquisition element 17 (step S1).

The observation-condition determining section 22 determines the observation conditions of the observation site X on the basis of the reference image acquired by the reference-image generating section 20; that is, it determines whether the observation site X is viewed from the front or from a parallel position (step S2). Then, based on the observation conditions of the observation site X, the preprocessing section 24 corrects the gradation values of the reference image acquired by the reference-image generating section 20 and the gradation values of the fluorescence image acquired by the fluorescence-image generating section 21.

Specifically, the observation-condition determining section 22 determines whether the observation site X is viewed from the front or whether the observation site X is viewed from a parallel position (step S3). Then, if it is determined that the observation site X is viewed from the front, an exponent y1 is set as the exponent y (step S4). If it is determined that the observation site X is viewed from a parallel position, an exponent y2 is set as the exponent y (step S5). The exponents y1 and y2 are set in advance in correspondence with the observation conditions of the observation site X.

Based on the exponent y set in this manner, the preprocessing section 24 corrects the gradation values of the reference image (step S6). Likewise, the exponent x is set in correspondence with the observation conditions of the observation site X. By using this exponent, the preprocessing section 24 corrects the gradation values of the fluorescence image acquired by the fluorescence-image generating section 21.

Subsequently, the fluorescence-image correcting section 25 divides the fluorescence image, whose gradation values have been corrected by the preprocessing section 24, by the reference image, whose gradation values have been corrected by the preprocessing section 24, so as to generate a corrected fluorescence image with a reduced variation in fluorescence intensity, which is dependent on the observation distance and the observation angle (step S7).

The image combining section 23 combines the corrected fluorescence image generated in this manner with the reference image acquired by the reference-image generating section 20, and these images are displayed side-by-side on a screen of the monitor 7 (step S8).

Because fluorescence and reflected light have different dependencies with respect to the observation distance and the observation angle, there is sometimes a case where, depending on the observation conditions, the effects of the observation distance and the observation angle cannot be completely compensated for even if the fluorescence image is divided by the reference image. In that case, the fluoroscopy device 1 according to this embodiment corrects the gradation values of the reference image and the fluorescence image on the basis of the observation conditions of the observation site X, whereby a sharp corrected fluorescence image with a reduced variation in fluorescence intensity, which is dependent on the observation distance and the observation angle, can be acquired.

For example, when the large intestine is observed, if the large intestine is viewed in a direction parallel to the axis thereof (parallel view), the gradation values in a central area of the reference image are low. On the other hand, if the large intestine is viewed in a direction intersecting the axis thereof (front view), the gradation values in the central area of the reference image are high. By determining whether the observation site X is viewed from the front or from a parallel position on the basis of the gradation values in the central area of the reference image, the gradation values of any one of the reference image and the fluorescence image can be corrected in accordance with the determination result, whereby a sharp corrected fluorescence image with a reduced variation in fluorescence intensity, which is dependent on the observation distance and the observation angle, can be acquired.

Furthermore, even when the observation conditions, such as the observation distance and the observation angle, change, the preprocessing section 24 can correct the gradation values of the reference image in accordance with the change in the observation conditions, whereby a sharp corrected fluorescence image with reduced effects of the change in the observation conditions can be acquired.

Specifically, gradation values F1 of the pixels in the fluorescence image and gradation values RL of the reference image are expressed as $FL \propto D^a \cos^b \theta$ and $RL \propto D^c \cos^d \theta$, respectively, and have different dependencies with respect to the distance and the angle. In this case, D denotes an observation distance, $\theta$ denotes an observation angle, and a, b, c, and d denote constants.

By raising the gradation values FL of the fluorescence image to the power of a certain exponent (first exponent) and raising the gradation values RL of the reference image to the power of a certain exponent (second exponent), a corrected fluorescence image with reduced dependencies on the observation distance and the observation angle can be acquired.

In this case, the preprocessing section 24 changes at least one of the first exponent and the second exponent in accordance with the observation conditions of the observation site X so that a reference image and a fluorescence image in which the dependencies on the observation distance and the observation angle are within an allowable error range can be obtained. Consequently, a sharp corrected fluorescence image with a reduced variation in fluorescence intensity, which is dependent on the observation distance and the observation angle, can be acquired.

As an alternative to the above-described embodiment in which the gradation values of the reference image $G_1$ and the fluorescence image $G_2$ are corrected by the preprocessing section 24, the gradation values of one of the reference image $G_1$ and the fluorescence image $G_2$ may be corrected. Specifically, when the corrected fluorescence image $G_3$ is to be generated by the fluorescence-image correcting section 25, the reference image $G_1'$ with corrected gradation values may be divided by the fluorescence image $G_2$ whose gradation values have not yet been corrected, or the reference image $G_1$ whose gradation values have not yet been corrected may be divided by the fluorescence image $G_2'$ with corrected gradation values.

Second Embodiment

Next, a fluoroscopy device 100 according to a second embodiment of the present invention will be described with reference to the drawings.

The fluoroscopy device 100 according to this embodiment differs from the fluoroscopy device 1 according to the first embodiment in that it corrects the gradation values of the corrected fluorescence image generated by dividing the fluorescence image by the reference image, instead of correcting the gradation values of the fluorescence image and the reference image. The following description regarding the fluoroscopy device 100 according to this embodiment does not include features thereof that are the same as those of the fluoroscopy device 1 according to the first embodiment and is mainly directed to features that are different therefrom.

Figure 9:
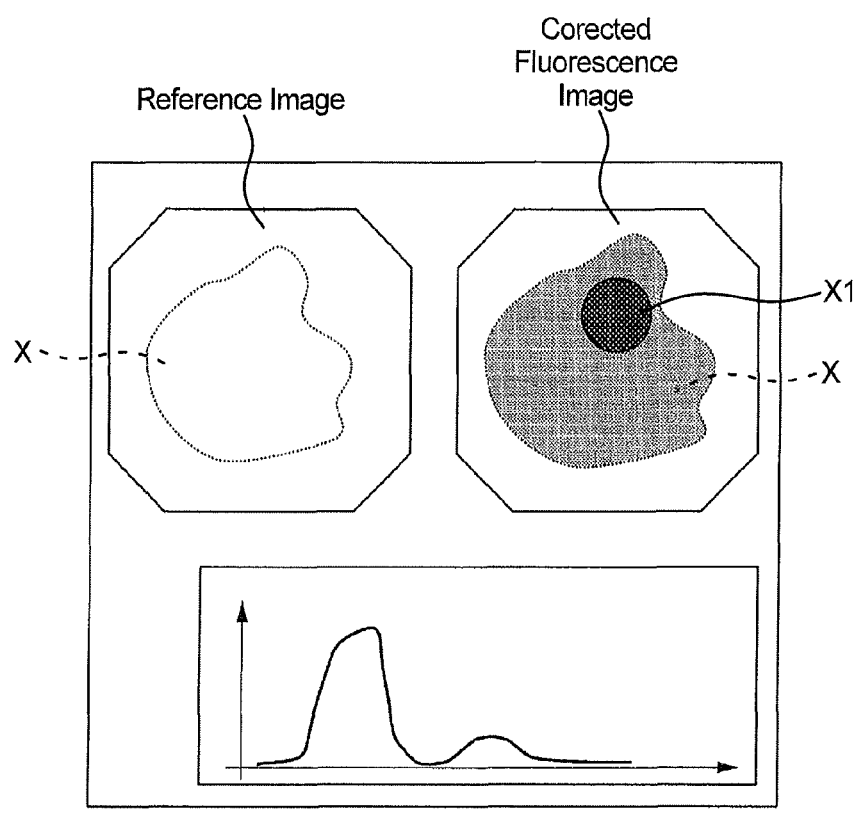
FIG. 9 illustrates examples of a reference image and a corrected fluorescence image and a histogram of gradation values of pixels in the corrected fluorescence image displayed on a monitor in FIG. 8 when a threshold value is not set.
Figure 10:
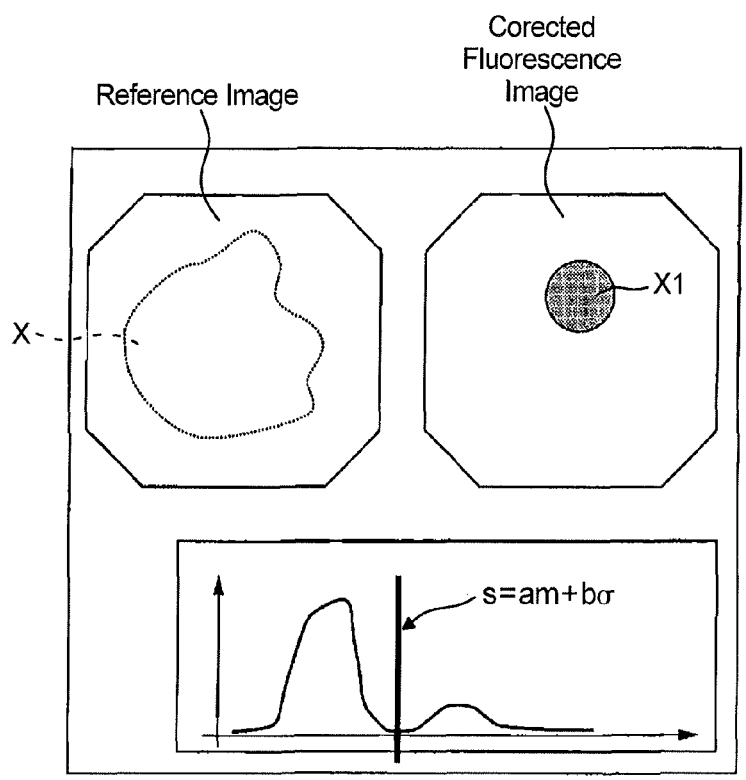
FIG. 10 illustrates examples of the reference image and the corrected fluorescence image and the histogram of gradation values of pixels in the corrected fluorescence image displayed on the monitor in FIG. 8 when a threshold value is set.

In order to observe the observation site X within the body cavity of a living organism by using the fluoroscopy device, a fluorescent agent, which preferentially accumulates in the lesion X1, such as cancer cells, is made to attach to or be absorbed in the observation site X. In this state, the observation site X is irradiated with excitation light so that the fluorescent agent is excited, whereby fluorescence is generated. In actuality, the fluorescent agent not only accumulates in the lesion X1 but also accumulates slightly in normal areas. Thus, weak fluorescence is also generated from areas other than the lesion X1 (i.e., background), as shown in FIG. 9. Therefore, as shown in FIG. 10, the fluoroscopy device 100 according to this embodiment sets an appropriate threshold value S for pixels of the corrected fluorescence image displayed on the monitor 7 and only displays pixels that are higher than the threshold value S.

Figure 8:
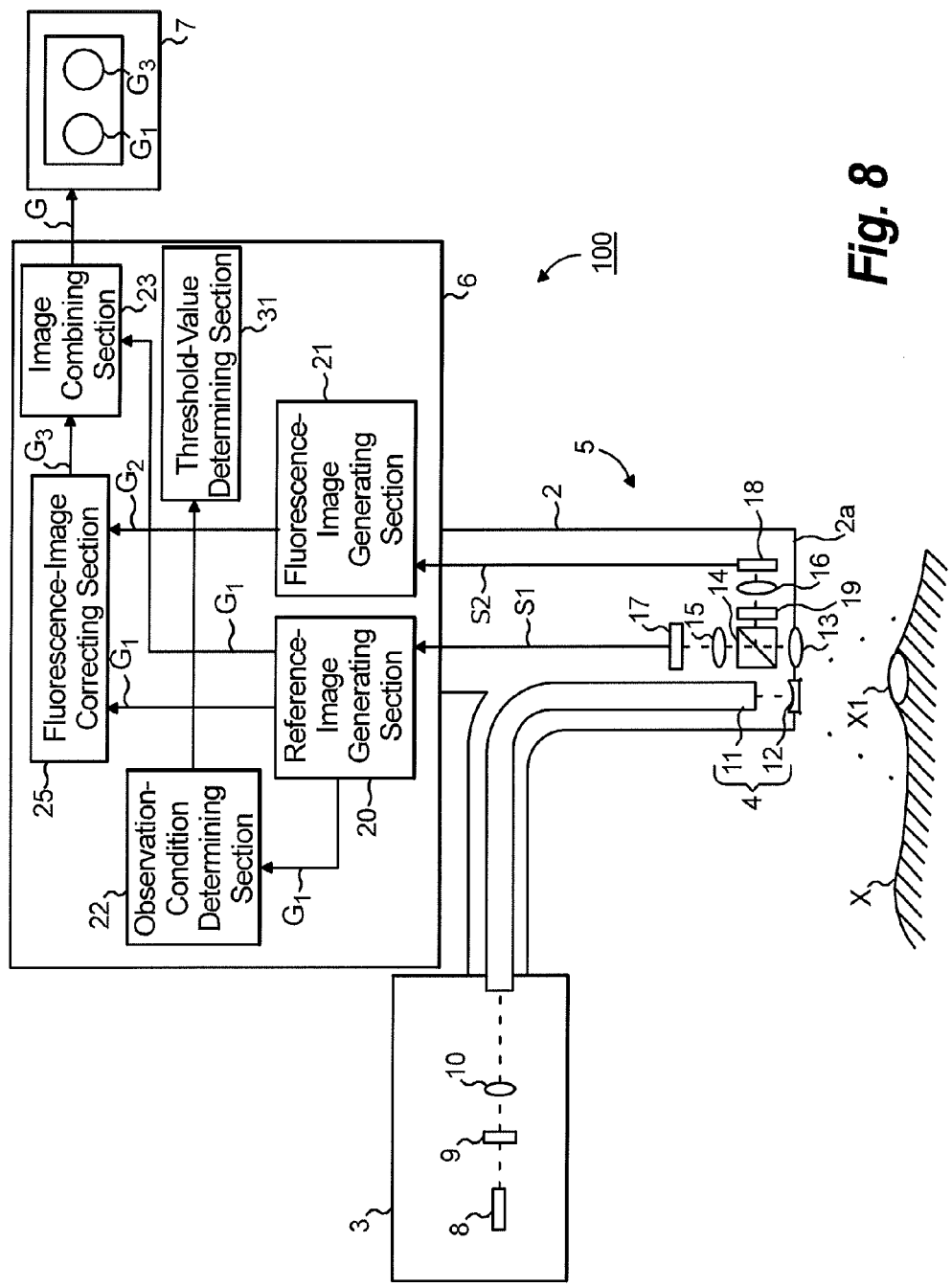
FIG. 8 schematically illustrates the configuration of a fluoroscopy device according to a second embodiment of the present invention.

As shown in FIG. 8, the image processing section 6 in the fluoroscopy device 100 according to this embodiment includes a reference-image generating section (reference-image acquisition section) 20 that generates a reference image $G_1$, a fluorescence-image generating section (fluorescence-image acquisition section) 21 that generates a fluorescence image $G_2$, an observation-condition determining section 22 that determines the observation conditions of the observation site X, a fluorescence-image correcting section 25 that generates a corrected fluorescence image $G_3$ from the reference image $G_1$ and the fluorescence image $G_2$, a threshold-value determining section (threshold-value setting section) 31 that determines a threshold value for the gradation values in the corrected fluorescence image, and an image combining section (image adjusting section) 23 that generates a combined image G by combining the corrected fluorescence image $G_3$ with the reference image $G_1$.

The fluorescence-image correcting section 25 divides the fluorescence image $G_2$ generated by the fluorescence-image generating section 21 by the reference image $G_1$ generated by the reference-image generating section 20 so as to generate the corrected fluorescence image $G_3$.

In accordance with the observation conditions of the observation site X determined by the observation-condition determining section 22, the threshold-value determining section 31 sets a threshold value S on the basis of the sum of an average gradation value m of the entire image and a standard deviation $\sigma$ respectively multiplied by predetermined coefficients a and b, as shown in the following computational equation (6):

$$S = am + b\sigma. \tag{6}$$

As mentioned above, the threshold value S is a value used for removing the background from the corrected fluorescence image.

Specifically, the threshold-value determining section 31 has a storage section (not shown) that stores the multiple coefficients a and b in correspondence with the observation conditions of the observation site X, and sets the threshold value S by selecting a coefficient a or b to be used from the multiple coefficients a and b stored in the storage section in accordance with the observation conditions of the observation site X determined by the observation-condition determining section 22.

The coefficients a and b may be set such that they decrease when an assumed percentage at which the lesion X1 occupies the corrected fluorescence image increases. A detailed description of how the coefficients a and b are set will be provided later.

The image combining section 23 combines the reference image $G_1$ generated by the reference-image generating section 20 with the corrected fluorescence image $G_3$ generated by the fluorescence-image correcting section 25. Specifically, for example, the image combining section 23 generates a combined image G in which the reference image $G_1$ and the corrected fluorescence image $G_3$ are arranged side-by-side, and outputs the combined image G to the monitor 7.

Furthermore, the image combining section 23 increases the contrast in the corrected fluorescence image between an area with pixels having gradation values larger than the threshold value S set by the threshold-value determining section 31 and an area with pixels having gradation values smaller than the threshold value S. Specifically, the image combining section 23 replaces the gradation values of pixels having gradation values smaller than the threshold value S in the corrected fluorescence image with zero.

A method of how the coefficients a and b in the above computational equation (6) are determined in the threshold-value determining section 31 will be described below with reference to a specific example.

The coefficients a and b are determined on the basis of, for example, an assumed average gradation value $m_1$ of the background and an assumed average gradation value $m_2$ of the lesion X1, and an assumed total number $n_1$ of pixels in the background and an assumed total number $n_2$ of pixels in the lesion X1, respectively.

The average gradation value m of the entire image is calculated by using, for example, the following computational equation (7):

$$m=(n_1 m_1+n_2 m_2)/(n_1+n_2). \qquad (7)$$

If the corrected fluorescence image has a total of 1,000,000 pixels, it is assumed that 950,000 pixels display the fluorescence from the background (total number $n_1$ of pixels corresponding to the background=950,000), and 50,000 pixels display the fluorescence from the lesion X1 (total number $n_2$ of pixels corresponding to the lesion X1=50,000). If the contrast of the fluorescent agent is 1:2, it is assumed that the average gradation value $m_1$ of the background is equal to 1000, and the average gradation value $m_2$ of the lesion X1 is equal to 2000.

The standard deviation σ of the entire image is calculated from the following computational equation (8):

$$\sigma = x^2 - m^2 \qquad (8)$$
$$= (n_1 x_1^2 + n_2 x_2^2)/(n_1+n_2) - m^2$$
$$= \frac{\{n_1(\sigma_1^2+m_1^2)+n_2(\sigma_2^2+m_2^2)\}}{(n_1+n_2)-m^2}.$$

In computational equation (8), $x^2$ denotes a square mean value of the gradation values of the entire image, $x_1^2$ denotes a square mean value of the gradation values of the background, $x_2^2$ denotes a square mean value of the gradation values of the lesion X1, $\sigma_1$ denotes a standard deviation of the gradation values of the pixels displaying the background, and $\sigma_2$ denotes a standard deviation of the gradation values of the pixels displaying the lesion X1.

Ideally, the standard deviation $\sigma_1$ of the background and the standard deviation $\sigma_2$ of the lesion X1 are both values close to the square root of the average gradation value. However, they change significantly due to fluctuations in the distribution of radiated light as well as the effects of protrusions and recesses on the surface of the observation site X. Assuming that each of the standard deviations $\sigma_1$ and $\sigma_2$ is ten times the ideal value (i.e., the square root of the average gradation value), the standard deviation $\sigma_1$ of the background is 316, and the standard deviation $\sigma_2$ of the lesion X1 is 447.

Even if fluorescence images with the same contrast are to be acquired, the average value of the gradation values increases as the area of the lesion X1 included in the image increases. Therefore, when acquiring fluorescence images with the same contrast, the values of appropriate coefficients a and b vary depending on the observation conditions. For example, even if a=1 and b=1 are appropriate at the normal observation distance, the area of the lesion X1 relatively increases with decreasing observation distance, resulting in a higher average value of the gradation values. Therefore, the values of appropriate coefficients a and b become smaller than those corresponding to the normal observation distance, such as 0.7 and 1, respectively.

Similar to the first embodiment, the observation-condition determining section 22 determines whether the observation site X is viewed from the front or from a parallel position. Since the observation distance is normally smaller when the observation site X is viewed from the front, the threshold-value determining section 31 sets the threshold value S by using a=1 and b=1 when it is determined that the observation site X is viewed from a parallel position, or by using a=0.7 and b=1 when it is determined that the observation site X is viewed from the front.

For example, when observing a relatively large protruding lesion, like a colon polyp, it can be assumed that the total number of pixels of the lesion X1 would increase since the lesion X1 would occupy a wide region of the corrected fluorescence image. Assuming that the total number $n_1$ of pixels of the background is 700,000 and the total number $n_2$ of pixels of the lesion X1 is 300,000, the average gradation value m of the entire image and the standard deviation σ of the entire image are calculated as follows on the basis of computational equations (7) and (8), respectively:

$$m=1300$$

$$\sigma=583.$$

In this case, when a=1 and b=1 are set, the threshold value S is calculated as follows on the basis of computational equation (6):

$$S=m+\sigma=1300+583=1883.$$

When this threshold value S is used, only 60.3% of the display of the lesion X1 is maintained. This is because the average value of the gradation values of the entire image is increased due to a large percentage at which the lesion X1 occupies the image, resulting in an excessively large threshold value.

When a=0.7 and b=1 are set, the threshold value S is calculated as follows on the basis of computational equation (6):

$$S=0.7m+\sigma=0.7\times1300+583=1493.$$

When this threshold value S is used, 87.1% of the lesion X1 is displayed, whereas 94.1% of the background is eliminated, whereby a sharper image can be acquired.

Accordingly, a minimum value and a maximum value for the threshold value S can be limited on the basis of the percentage at which an area having pixels with high gradation values occupies the corrected fluorescence image. Therefore, the threshold value S is prevented from becoming too high even when the average value of the gradation values increases due to the lesion X1 occupying a wide region of the corrected fluorescence image, whereby the display of the lesion X1 is prevented from being suppressed. On the other hand, the threshold value S is prevented from becoming too low even when the average value of the gradation values decreases due to an area with low gradation values occupying a wide region of the corrected fluorescence image, whereby the display of the background is prevented from being emphasized.

Figure 11:
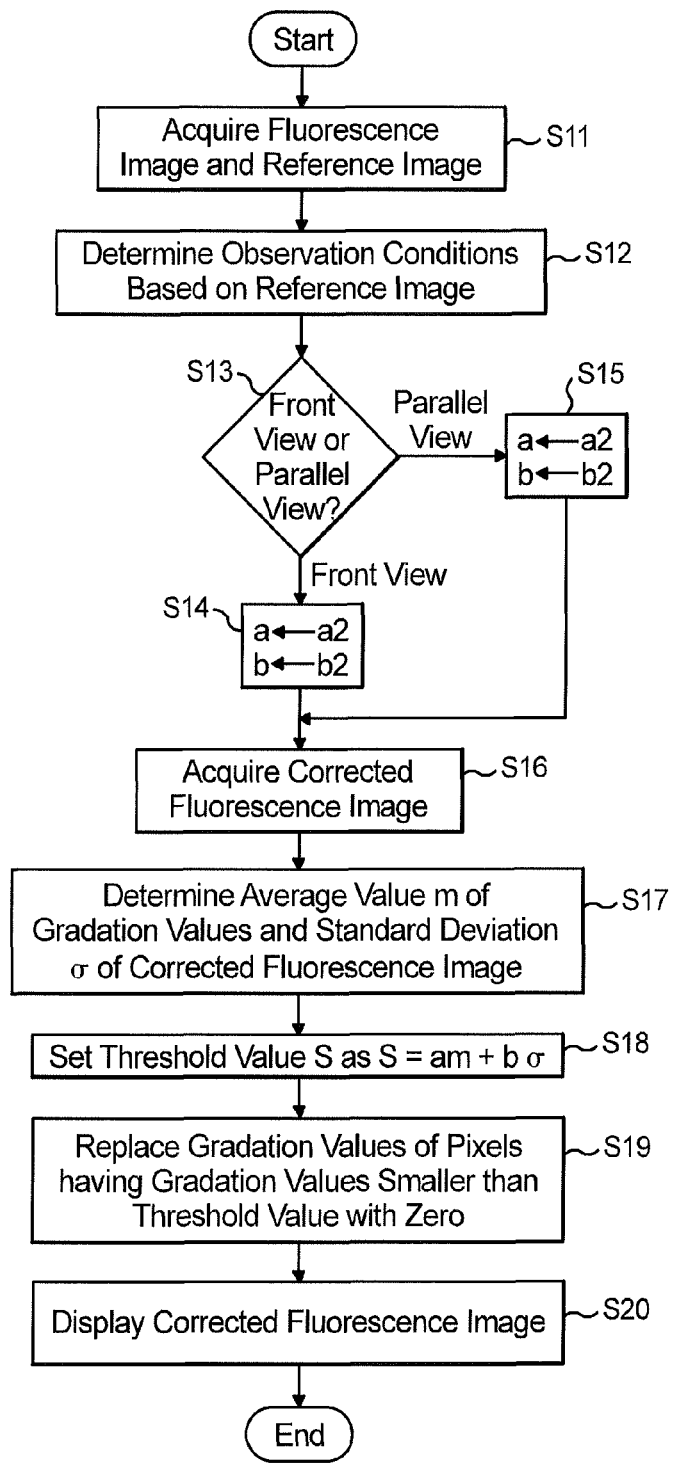
FIG. 11 is a flowchart illustrating a process performed by an image processing section in FIG. 8.

The operation of the fluoroscopy device 100 having the above-described configuration will be described below with reference to a flowchart shown in FIG. 11.

Since the process from the step of inserting the insertion section 2 into the body cavity and irradiating the observation site X with white light including excitation light to the step of acquiring reference-image information and fluorescence-image information with the image acquisition elements 17 and 18 is the same as that in the first embodiment, a description thereof will be omitted.

A two-dimensional fluorescence image is generated in the fluorescence-image generating section 21 on the basis of the fluorescence-image information transmitted from the image acquisition element 18, and a two-dimensional reference image is generated in the reference-image generating section 20 on the basis of the reference-image information transmitted from the image acquisition element 17 (step S11).

The observation-condition determining section 22 determines the observation conditions of the observation site X on the basis of the reference image acquired by the reference-image generating section 20; that is, it determines whether the observation site X is viewed from the front or from a parallel position (step S12).

Specifically, the observation-condition determining section 22 determines whether the observation site X is viewed from the front or from a parallel position (step S13). Then, if it is determined that the observation site X is viewed from the front, the coefficient a is set equal to a1, and the coefficient b is set equal to b1 (step S14). If it is determined that the observation site X is viewed from a parallel position, the coefficient a is set equal to a2, and the coefficient b is set equal to b2 (step S15). The values a1, a2, b1, and b2 are predetermined coefficients set in correspondence with the observation conditions of the observation site X.

Subsequently, the fluorescence-image correcting section 25 divides the fluorescence image acquired by the fluorescence-image generating section 21 by the reference image acquired by the reference-image generating section 20 so as to generate a corrected fluorescence image with a reduced variation in fluorescence intensity, which is dependent on the observation distance and the observation angle (step S16).

Then, an average gradation value m of the entire corrected fluorescence image generated in this manner and a standard deviation σ of the entire image are calculated on the basis of the aforementioned computational equations (7) and (8) (step S17).

Subsequently, based on the aforementioned computational equation (6), a threshold value S is calculated from the calculated coefficients a and b, the average gradation value m of the entire image, and the standard deviation σ of the entire image (step S18).

Then, the contrast in the corrected fluorescence image between an area with pixels having gradation values larger than the threshold value S set by the threshold-value determining section 31 and an area with pixels having gradation values smaller than the threshold value S is increased (step S19). Specifically, the gradation values of pixels having gradation values smaller than the threshold value S in the corrected fluorescence image are replaced with zero.

The corrected fluorescence image in which the gradation values of pixels having gradation values smaller than the threshold value S are replaced with zero is displayed on the monitor 7 (step S20).

Accordingly, with the fluoroscopy device 100 according to this embodiment, the threshold-value determining section 31 sets the threshold value S on the basis of the average value of the gradation values of the pixels in the corrected fluorescence image, so that the contrast in the corrected fluorescence image between an area having gradation values larger than the threshold value and an area having gradation values smaller than the threshold value is increased. Consequently, a sharp corrected fluorescence image with reduced effects of weak fluorescence generated from the background can be acquired.

In this case, when the lesion X1 and the normal areas are to be distinguished from each other based on the threshold value S, as described above, the accuracy of distinguishing the lesion X1 and the normal areas from each other may change depending on the observation conditions. By changing the threshold value S in accordance with the observation conditions of the observation site X so as to correct the gradation values of the corrected fluorescence image, a sharp corrected fluorescence image with a reduced variation in fluorescence intensity, which is dependent on the observation distance and the observation angle, can be acquired, regardless of the observation conditions.

For example, when the large intestine is observed, if the large intestine is viewed in a direction parallel to the axis thereof (parallel view), the gradation values in a central area of the reference image are low. On the other hand, if the large intestine is viewed in a direction intersecting the axis thereof (front view), the gradation values in the central area of the reference image are high. By determining whether the observation site X is viewed from the front or from a parallel position on the basis of the gradation values in the central area of the reference image, the gradation values of the corrected fluorescence image can be corrected in accordance with the determination result, whereby a sharp corrected fluorescence image with a reduced variation in fluorescence intensity, which is dependent on the observation distance and the observation angle, can be acquired.

In this embodiment, the image combining section 23 eliminates the display of fluorescence from the background and maintains the display of the lesion X1. Alternatively, for example, the gradation values of the pixels displaying the background may be reduced to an extent that the display of the background is not eliminated, and the gradation values of the pixels displaying the lesion X1 may be increased, so long as the contrast between the fluorescence from the lesion X1 and the fluorescence from the background can be increased.

Third Embodiment

Next, a fluoroscopy device 101 according to a third embodiment of the present invention will be described with reference to the drawings.

The fluoroscopy device 101 differs from the fluoroscopy devices 1 and 100 according to the above-described embodiments in that it removes a high-frequency component of the reference image by using a low-pass filter. The following description regarding the fluoroscopy device 101 according to this embodiment does not include features thereof that are the same as those of the fluoroscopy devices 1 and 100 according to the above-described embodiments and is mainly directed to features that are different therefrom.

If the reference image acquired by the reference-image generating section 20 contains non-distance-related information, such as blood vessels, edges, and shadows, the fluorescence image would be divided by the reference image that contains components that are not related to the distance, possibly causing noise. The fluoroscopy device 101 according to this embodiment uses a low-pass filter to block a predetermined high-frequency component in the reference image so as to acquire a sharp reference image from which a noise component is removed, whereby a sharp corrected fluorescence image can be acquired by using this reference image.

However, although the aforementioned non-distance-related information, such as blood vessels, edges, and shadows, can be eliminated by lowering the frequency band (cut-off frequency) to be removed by the low-pass filter, this results in a loss of accuracy since the reference image becomes far from its original image. In other words, the cut-off frequency is desirably set to a value based on which a component that causes noise can be sufficiently blocked while the accuracy of the image can be maintained as much as possible.

Figure 12:
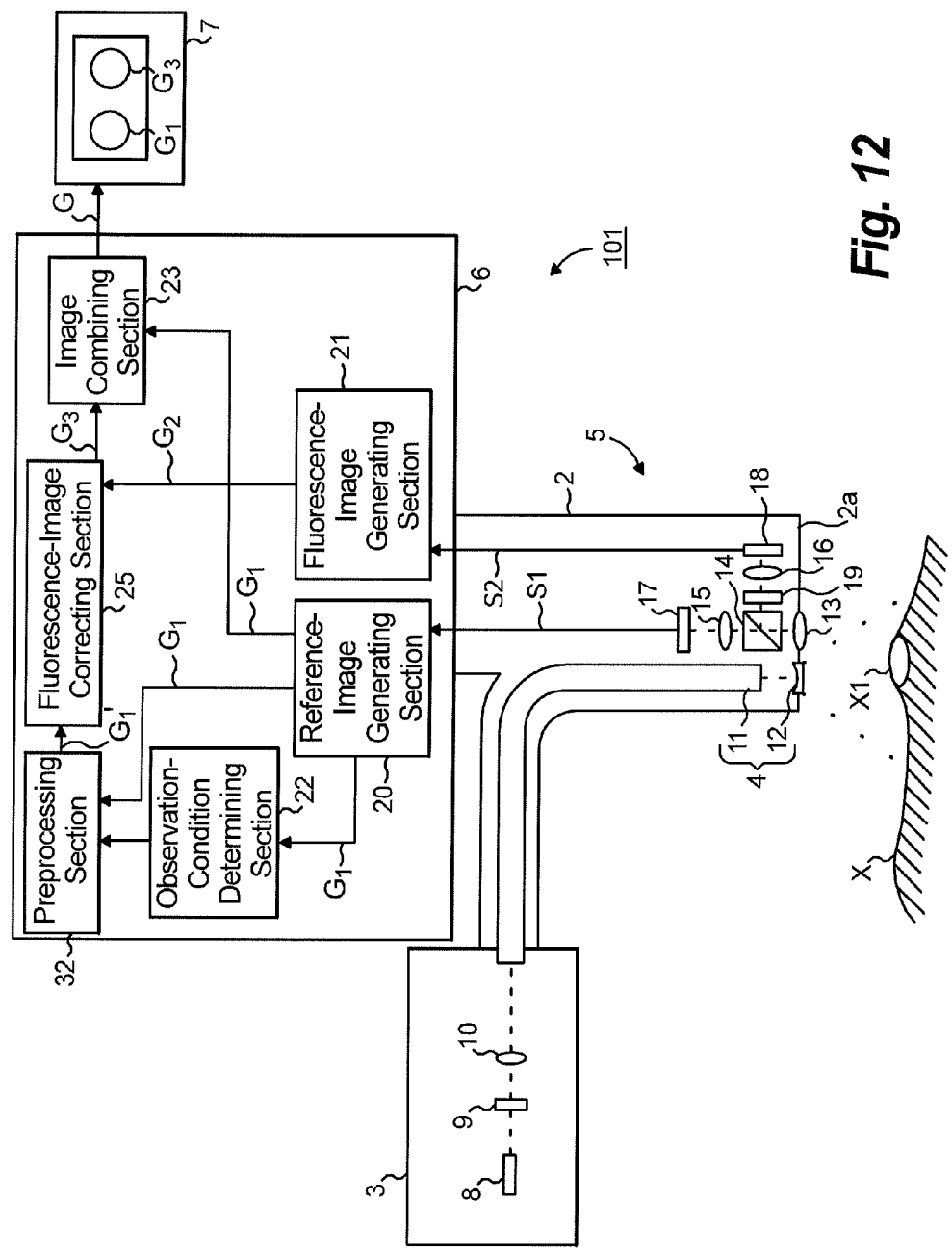
FIG. 12 schematically illustrates the configuration of a fluoroscopy device according to a third embodiment of the present invention.

As shown in FIG. 12, the image processing section 6 in the fluoroscopy device 101 according to this embodiment includes a reference-image generating section (reference-image acquisition section) 20 that generates a reference image $G_1$, a fluorescence-image generating section (fluorescence-image acquisition section) 21 that generates a fluorescence image $G_2$, an observation-condition determining section 22 that determines the observation conditions of the observation site X, a fluorescence-image correcting section 25 that generates a corrected fluorescence image $G_3$ from the reference image $G_1$ and the fluorescence image $G_2$, a preprocessing section 32 that removes a high-frequency component from the reference image $G_1$, and an image combining section 23 that generates a combined image G by combining the corrected fluorescence image $G_3$ with the reference image $G_1'$.

The preprocessing section 32 includes a low-pass filter (not shown) that blocks a high-frequency component in the reference image acquired by the reference-image generating section 20, and a cut-off-frequency adjusting section (not shown) that adjusts the cut-off frequency of the low-pass filter in accordance with the observation conditions of the observation site X determined by the observation-condition determining section 22.

With the above configuration, the preprocessing section 32 can change the frequency band to be blocked by the low-pass filter in accordance with the observation conditions of the observation site X.

When the observation-condition determining section 22 determines that the observation site X is viewed from the front, for example, a wall surface of the large intestine is being viewed. In this case, since an image of blood vessels or the like tends to appear in the reference image, the cut-off frequency of the low-pass filter is set to a low value. On the other hand, when the observation-condition determining section 22 determines that the observation site X is viewed from a parallel position, the observation site X is normally viewed from a far position. In this case, since an image of blood vessels or the like does not often occupy a large area of the reference image, the cut-off frequency of the low-pass filter is set to a high value.

Figure 13:
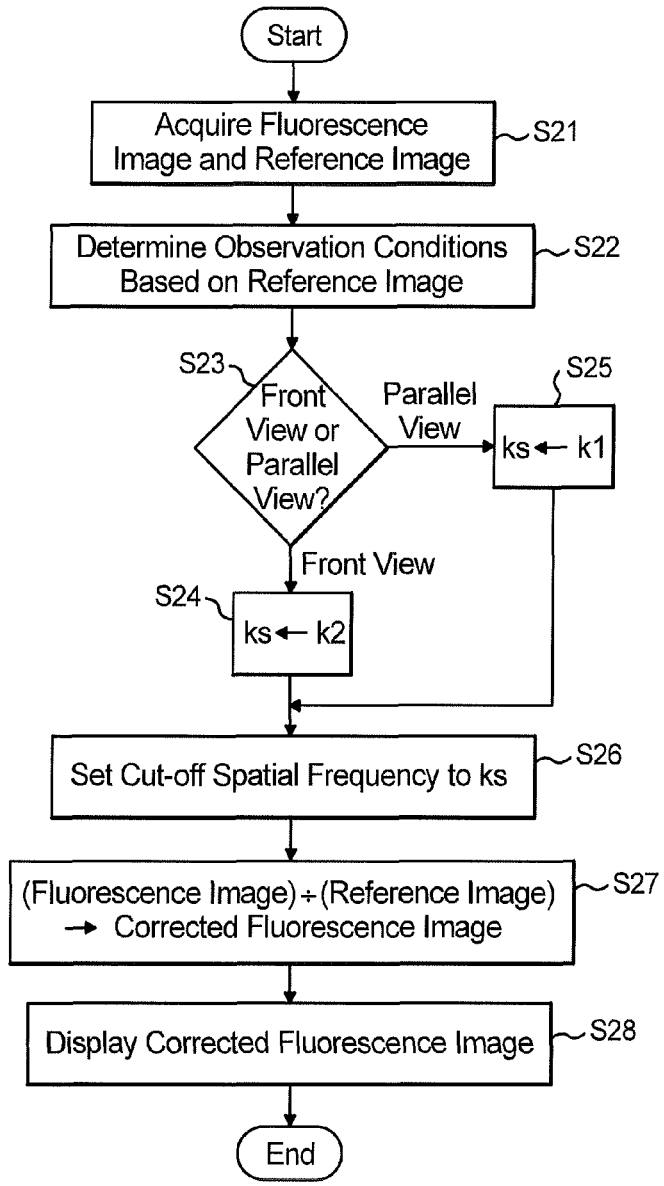
FIG. 13 is a flowchart illustrating a process performed by an image processing section in FIG. 12.

The operation of the fluoroscopy device 101 having the above-described configuration will be described below with reference to a flowchart shown in FIG. 13.

Since the process from the step of inserting the insertion section 2 into the body cavity and irradiating the observation site X with white light including excitation light to the step of acquiring reference-image information and fluorescence-image information with the image acquisition elements 17 and 18 is the same as that in the first embodiment, a description thereof will be omitted.

A two-dimensional fluorescence image is generated in the fluorescence-image generating section 21 on the basis of the fluorescence-image information transmitted from the image acquisition element 18, and a two-dimensional reference image is generated in the reference-image generating section 20 on the basis of the reference-image information transmitted from the image acquisition element 17 (step S21).

The observation-condition determining section 22 determines the observation conditions of the observation site X on the basis of the reference image acquired by the reference-image generating section 20; that is, it determines whether the observation site X is viewed from the front or from a parallel position (step S22).

Specifically, the observation-condition determining section 22 determines whether the observation site X is viewed from the front or from a parallel position (step S23). Then, if it is determined that the observation site X is viewed from the front, a cut-off frequency ks is set equal to k2 (step S24). If it is determined that the observation site X is viewed from a parallel position, the cut-off frequency ks is set equal to k1 (step S25). The values k1 and k2 are predetermined cut-off frequencies set in correspondence with the observation conditions of the observation site X.

Subsequently, the preprocessing section 32 applies the selected low-pass filter to the reference image acquired by the reference-image generating section 20 (step S26).

Then, the fluorescence-image correcting section 25 divides the fluorescence image acquired by the fluorescence-image generating section 21 by the reference image to which the low-pass filter is applied by the preprocessing section 32 so as to generate a corrected fluorescence image with a reduced variation in fluorescence intensity, which is dependent on the observation distance and the observation angle (step S27).

The corrected fluorescence image generated in this manner is displayed on the monitor 7 (step S28).

Accordingly, although the appearance of the blood vessels, the edges, and the like in the reference image may change depending on the observation conditions, the fluoroscopy device 101 according to this embodiment changes the frequency band to be blocked by the low-pass filter in accordance with the observation conditions of the observation site X, so that a sharp corrected fluorescence image can be acquired, regardless of the observation conditions.

In this embodiment, the preprocessing section 32 may include multiple low-pass filters (not shown) that block predetermined high-frequency components in the reference image acquired by the reference-image generating section 20, and a selecting section (not shown) that selects a low-pass filter suitable for the observation conditions from among the multiple low-pass filters in accordance with the observation conditions of the observation site X determined by the observation-condition determining section 22.

With the above configuration, the preprocessing section 32 can change the frequency band to be blocked by the low-pass filter in accordance with the observation conditions of the observation site X.

Fourth Embodiment

Next, a fluoroscopy device 102 according to a fourth embodiment of the present invention will be described with reference to the drawings.

The fluoroscopy device 102 according to this embodiment changes the criterion for the determination of the observation conditions of the observation site X by the observation-condition determining section 22 for each scope (insertion section). With regard to the fluoroscopy device 102 according to this embodiment, a modification of the fluoroscopy device 100 according to the second embodiment will be described below as an example.

Figure 14:
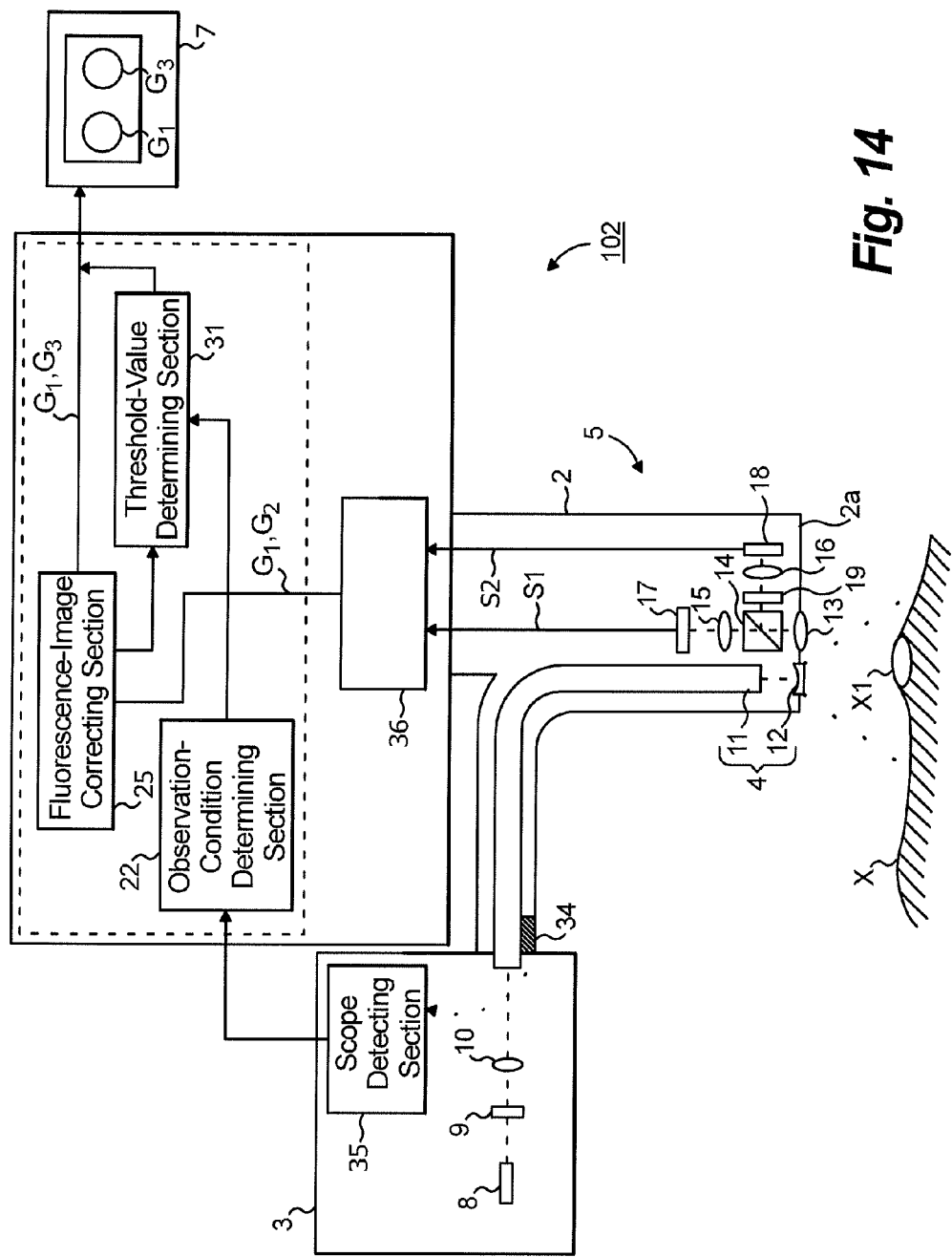
FIG. 14 schematically illustrates the configuration of a fluoroscopy device according to a fourth embodiment of the present invention.

As shown in FIG. 14, the fluoroscopy device 102 according to this embodiment is configured such that the insertion section 2 is attachable to and detachable from the fluoroscopy device 102. The insertion section 2 is provided with an IC chip 34 that stores identification information of the insertion section 2.

The light source 3 is provided with a scope detecting section 35 that reads the identification information stored in the IC chip 34 so as to detect the identification information of the insertion section 2.

In the scope detecting section 35, insertion-section information is preliminarily stored in correspondence with the identification information of the insertion section. The insertion-section information includes, for example, the number of illumination units 4 constituted of the light guide fiber 11 and the illumination optical system 12, an observation angle between the illumination units 4 and a light receiving section constituted of the objective lens 13, and the like.

In the fluoroscopy device 102 having the above configuration, when the insertion section 2 is connected to the light source 3, the scope detecting section 35 reads the identification information of the insertion section 2 stored in the IC chip 34 and transmits the information about the insertion section 2 preliminarily stored in correspondence with the identification information to the observation-condition determining section 22. In the observation-condition determining section 22, the coefficients a and b are selected on the basis of the information about the insertion section 2.

Because the observation magnification and the like vary depending on the type of the insertion section 2, the total number $n_1$ of pixels of the background and the total number $n_2$ of pixels of the lesion X1 vary even if the same lesion X1 is observed. In this case, with the fluoroscopy device 102 according to this embodiment, threshold values corresponding to various types of insertion sections with different specifications and purposes can be set.

Although the identification information of the insertion section 2 is stored in the IC chip 34, and the information about the insertion section 2, such as the number of illumination units 4, is stored in the scope detecting section 35 in the above description, the information about the insertion section 2, such as the number of illumination units 4, may alternatively be stored in the IC chip 34.

Furthermore, although the modification of the fluoroscopy device 100 according to the second embodiment is described in this embodiment, this embodiment may also be applied to the fluoroscopy devices 1 and 101 according to the first and third embodiments. Specifically, in the first and third embodiments, the identification information of the insertion section 2 may be read, and the exponent y and the cut-off frequency ks may be changed on the basis of the identification information.

Although the embodiments of the present invention have been described above in detail with reference to the drawings, the specific configurations are not limited to those in the above embodiments and may include other design modifications so long as they do not depart from the scope of the invention. For example, the present invention is not limited to the above embodiments and modifications thereof, and may be applied to an embodiment with an appropriate combination of the embodiments and the modifications thereof; the invention is not limited in particular.

REFERENCE SIGNS LIST

X observation site
X1 lesion
1, 100, 101, 102 fluoroscopy device
2 insertion section
3 light source
4 illumination unit
5 image acquisition unit
6 image processing section
7 monitor
20 reference-image generating section (reference-image acquisition section)
21 fluorescence-image generating section (fluorescence-image acquisition section)
22 observation-condition determining section
23 image combining section (image adjusting section)
24 preprocessing section (gradation-value correcting section)
25 fluorescence-image correcting section (corrected-fluorescence-image generating section)
31 threshold-value determining section (threshold-value setting section)
32 preprocessing section (gradation-value correcting section)

The invention claimed is:

1. A fluoroscopy device comprising:
a light source that irradiates a subject with excitation light and reference light;
a fluorescence-image acquisition section that acquires a fluorescence image by capturing fluorescence generated in the subject irradiated with the excitation light from the light source;
a reference-image acquisition section that acquires a reference image by capturing return light returning from the subject irradiated with the reference light from the light source;
an observation-condition determining section that determines an observation condition of the subject on the basis of the reference image acquired by the reference-image acquisition section;
a gradation-value correcting section that corrects gradation values of the reference image acquired by the reference-image acquisition section on the basis of the observation condition of the subject determined by the observation-condition determining section; and
a corrected-fluorescence-image generating section that generates a corrected fluorescence image by dividing the fluorescence image acquired by the fluorescence-image acquisition section by the reference image whose gradation values have been corrected by the gradation-value correcting section.

2. A fluoroscopy device comprising:
a light source that irradiates a subject with excitation light and reference light;
a fluorescence-image acquisition section that acquires a fluorescence image by capturing fluorescence generated in the subject irradiated with the excitation light from the light source;
a reference-image acquisition section that acquires a reference image by capturing return light returning from the subject irradiated with the reference light from the light source;
an observation-condition determining section that determines an observation condition of the subject on the basis of the reference image acquired by the reference-image acquisition section;
a gradation-value correcting section that corrects gradation values of the fluorescence image acquired by the fluorescence-image acquisition section on the basis of the observation condition of the subject determined by the observation-condition determining section; and
a corrected-fluorescence-image generating section that generates a corrected fluorescence image by dividing the fluorescence image, whose gradation values have been corrected by the gradation-value correcting section, by the reference image acquired by the reference-image acquisition section.

3. A fluoroscopy device comprising:
a light source that irradiates a subject with excitation light and reference light;
a fluorescence-image acquisition section that acquires a fluorescence image by capturing fluorescence generated in the subject irradiated with the excitation light from the light source;
a reference-image acquisition section that acquires a reference image by capturing return light returning from the subject irradiated with the reference light from the light source;
an observation-condition determining section that determines an observation condition of the subject on the basis of the reference image acquired by the reference-image acquisition section;
a gradation-value correcting section that corrects gradation values of the reference image acquired by the reference-image acquisition section and the fluorescence image acquired by the fluorescence-image acquisition section on the basis of the observation condition of the subject determined by the observation-condition determining section; and
a corrected-fluorescence-image generating section that generates a corrected fluorescence image by dividing the fluorescence image, whose gradation values have been corrected by the gradation-value correcting section, by the reference image whose gradation values have been corrected by the gradation-value correcting section.

4. A fluoroscopy device comprising:
a light source that irradiates a subject with excitation light and reference light;
a fluorescence-image acquisition section that acquires a fluorescence image by capturing fluorescence generated in the subject irradiated with the excitation light from the light source;
a reference-image acquisition section that acquires a reference image by capturing return light returning from the subject irradiated with the reference light from the light source;
a corrected-fluorescence-image generating section that generates a corrected fluorescence image by dividing the fluorescence image acquired by the fluorescence-image acquisition section by the reference image acquired by the reference-image acquisition section;
an observation-condition determining section that determines an observation condition of the subject on the basis of the reference image acquired by the reference-image acquisition section; and
a gradation-value correcting section that corrects gradation values of the corrected fluorescence image generated by the corrected-fluorescence-image generating section on the basis of the observation condition of the subject determined by the observation-condition determining section.

5. The fluoroscopy device according to claim 1,
wherein the gradation-value correcting section changes at least one of a first exponent and a second exponent in accordance with the observation condition of the subject determined by the observation-condition determining section, the first exponent corresponding to gradation values of the fluorescence image acquired by the fluorescence-image acquisition section when the subject is irradiated with the excitation light and being obtained by power approximation of distance characteristics from the light source to the subject, the second exponent corresponding to gradation values of the reference image acquired by the reference-image acquisition section when the subject is irradiated with the reference light and being obtained by power approximation of the distance characteristics from the light source to the subject.

6. The fluoroscopy device according to claim 2,
wherein the gradation-value correcting section changes at least one of a first exponent and a second exponent in accordance with the observation condition of the subject determined by the observation-condition determining section, the first exponent corresponding to gradation values of the fluorescence image acquired by the fluorescence-image acquisition section when the subject is irradiated with the excitation light and being obtained by power approximation of distance characteristics from the light source to the subject, the second exponent corresponding to gradation values of the reference image acquired by the reference-image acquisition section when the subject is irradiated with the reference light and being obtained by power approximation of the distance characteristics from the light source to the subject.

7. The fluoroscopy device according to claim 3,
wherein the gradation-value correcting section changes at least one of a first exponent and a second exponent in accordance with the observation condition of the subject determined by the observation-condition determining section, the first exponent corresponding to gradation values of the fluorescence image acquired by the fluorescence-image acquisition section when the subject is irradiated with the excitation light and being obtained by power approximation of distance characteristics from the light source to the subject, the second exponent corresponding to gradation values of the reference image acquired by the reference-image acquisition section when the subject is irradiated with the reference light and being obtained by power approximation of the distance characteristics from the light source to the subject.

8. The fluoroscopy device according to claim 4,
wherein the gradation-value correcting section includes
a threshold-value setting section that sets a threshold value on the basis of an average value of the gradation values of pixels in the corrected fluorescence image generated by the corrected-fluorescence-image generating section, and
an image adjusting section that increases the contrast in the corrected fluorescence image between an area having gradation values larger than the threshold value and an area having gradation values smaller than the threshold value, and
wherein the threshold value is changed in accordance with the observation condition of the subject determined by the observation-condition determining section.

9. The fluoroscopy device according to claim 1,
wherein the gradation-value correcting section includes a low-pass filter that blocks a high-frequency component in the reference image acquired by the reference-image acquisition section, and
wherein a frequency band to be blocked by the low-pass filter is changed in accordance with the observation condition of the subject.

10. The fluoroscopy device according to claim 1,
wherein the observation-condition determining section determines that the subject is viewed from a parallel position if gradation values of a central area in the reference image are smaller than or equal to a predetermined value, or determines that the subject is viewed from the front if the gradation values of the central area in the reference image are larger than the predetermined value.

11. The fluoroscopy device according to claim 2,
wherein the observation-condition determining section determines that the subject is viewed from a parallel position if gradation values of a central area in the reference image are smaller than or equal to a predetermined value, or determines that the subject is viewed from the front if the gradation values of the central area in the reference image are larger than the predetermined value.

12. The fluoroscopy device according to claim 3,
wherein the observation-condition determining section determines that the subject is viewed from a parallel position if gradation values of a central area in the reference image are smaller than or equal to a predetermined value, or determines that the subject is viewed from the front if the gradation values of the central area in the reference image are larger than the predetermined value.

13. The fluoroscopy device according to claim 4,
wherein the observation-condition determining section determines that the subject is viewed from a parallel position if gradation values of a central area in the reference image are smaller than or equal to a predetermined value, or determines that the subject is viewed from the front if the gradation values of the central area in the reference image are larger than the predetermined value.

14. The fluoroscopy device according to claim 1,
wherein the gradation-value correcting section includes a storage section that stores a plurality of correction coefficients in correspondence with the observation condition of the subject, and
wherein a correction coefficient to be used is selected from among the plurality of correction coefficients stored in the storage section in accordance with the observation condition of the subject determined by the observation-condition determining section so as to correct gradation values of at least one of the reference image, the fluorescence image, and the corrected fluorescence image.

15. The fluoroscopy device according to claim 2,
wherein the gradation-value correcting section includes a storage section that stores a plurality of correction coefficients in correspondence with the observation condition of the subject, and
wherein a correction coefficient to be used is selected from among the plurality of correction coefficients stored in the storage section in accordance with the observation condition of the subject determined by the observation-condition determining section so as to correct gradation values of at least one of the reference image, the fluorescence image, and the corrected fluorescence image.

16. The fluoroscopy device according to claim 3,
wherein the gradation-value correcting section includes a storage section that stores a plurality of correction coefficients in correspondence with the observation condition of the subject, and
wherein a correction coefficient to be used is selected from among the plurality of correction coefficients stored in the storage section in accordance with the observation condition of the subject determined by the observation-condition determining section so as to correct gradation values of at least one of the reference image, the fluorescence image, and the corrected fluorescence image.

17. The fluoroscopy device according to claim 4,
wherein the gradation-value correcting section includes a storage section that stores a plurality of correction coefficients in correspondence with the observation condition of the subject, and
wherein a correction coefficient to be used is selected from among the plurality of correction coefficients stored in the storage section in accordance with the observation condition of the subject determined by the observation-condition determining section so as to correct gradation values of at least one of the reference image, the fluorescence image, and the corrected fluorescence image.

\* \* \* \* \*